United States Patent [19]

Hiratsuka et al.

[11] 4,128,470
[45] Dec. 5, 1978

[54] SUPPORTS FOR ELECTROPHORESIS AND PROCESS FOR THE PRODUCTION OF THE SAME

[75] Inventors: Nobuo Hiratsuka; Nakatsugu Yaginuma, both of Minami-ashigara, Japan

[73] Assignee: Fuji Photo Film Co., Ltd., Minami-ashigara, Japan

[21] Appl. No.: 879,421

[22] Filed: Feb. 21, 1978

Related U.S. Application Data

[63] Continuation of Ser. No. 718,505, Aug. 30, 1976, abandoned.

[30] Foreign Application Priority Data

Aug. 29, 1975 [JP] Japan ................. 50-104725

[51] Int. Cl.$^2$ .................. G01N 27/26; G01N 27/28
[52] U.S. Cl. .................. 204/299 R; 204/180 S; 210/500 M; 264/41
[58] Field of Search .......... 204/180 S, 180 G, 299 R; 23/253 R, 253 TP, 230 B; 210/500 M; 264/41; 210/23; 161/160

[56] References Cited

U.S. PATENT DOCUMENTS

| | | | |
|---|---|---|---|
| 1,421,341 | 6/1922 | Zsigmondy | 210/500 M |
| 2,944,017 | 7/1960 | Cotton | 210/500 M |
| 3,439,074 | 4/1969 | Sharples et al. | 264/41 |
| 3,556,992 | 1/1971 | Massuco | 210/63 |
| 3,592,953 | 7/1971 | Ward et al. | 210/500 M X |
| 3,594,263 | 7/1971 | Dwyer et al. | 161/160 |
| 3,808,118 | 4/1974 | Golias | 204/180 S X |
| 3,857,778 | 12/1974 | Hiratsuka et al. | 204/299 R |
| 3,960,499 | 6/1976 | White | 204/299 R X |

*Primary Examiner*—Arthur C. Prescott
*Attorney, Agent, or Firm*—Sughrue, Rothwell, Mion, Zinn and Macpeak

[57] ABSTRACT

A support for electrophoresis comprising a porous polymer film having an electroendosmosis factor of 0 to plus about 10 mm, and a process for the production of the support comprising adding a nonionic surface active agent and/or cellulose ether to a mixed solution comprising at least a polymer material for formation of a film and a solvent to produce a porous polymer film.

9 Claims, 3 Drawing Figures

SUPPORTS FOR ELECTROPHORESIS AND PROCESS FOR THE PRODUCTION OF THE SAME

BACKGROUND OF THE INVENTION

This is a continuation of application Ser. No. 718,505, filed Aug. 30, 1976, now abandoned.

FIELD OF THE INVENTION

The present invention relates to a support for electrophoresis and a process for the production of the same. More particularly, the present invention provides a support suitable for isoelectric focusing and a process for the production of the same.

DESCRIPTION OF THE PRIOR ART

Electrophoresis is used for the separation and purification of charged particles, and it is particularly useful for the separation and fractionation of proteins. Electrophoretic processes include, in addition to general electrophoretic processes, a disc electrophoretic process in which separation is carried out using a discontinuous buffer solution system, an immunoelectrophoretic process in which separation and detection are carried out via an immunodiffusion reaction, and an isoelectric focusing process in which a pH gradient is formed between electrodes, and separation and fractionation are carried out in this pH gradient, etc.

In isoelectric focusing, as described above, a pH gradient is formed between electrodes, and ampholytes such as proteins and the like are separated and fractionated in this pH gradient, and since the proteins, etc., are concentrated at the position of the pH of the isoelectric point, the fractionation is very sharp, and, thus, in regard to resolving power, this method is the best of the electrophoretic processes. Furthermore, as compared with the conventional electrophoretic processes in which it is difficult to determine the isoelectric point, in isoelectric focusing it is easy to determine the isoelectric point.

Isoelectric focusing further has the advantages that the fractionated zone of the proteins, etc., does not move from the position of the isoelectric point, and in that because of the action of the force of electrically focusing, the sharpness of the separated zone is free from deterioration due to diffusion. Moreover, unlike conventional electrophoretic processes, it is not necessary to use different specific buffer solutions depending upon enzymes, and, thus, it is possible to effect fractionation under the same conditions using a carrier ampholyte having the desired pH range.

Isoelectric focusing involves a method in which fractionation is carried out in a solution in a column, and a method in which a polyacrylamide gel thin layer is used as a support. The former method in which fractionation is carried out in a column is excellent for fractionation and separation because it makes it possible to fractionate a large quantity of the sample. This method, however, is not suitable as an analytical method in that since only one sample can be fractionated at one time and a large quantity of carrier ampholyte is needed, the cost required for operation increases, and a long period of time is needed for the fractionation.

On the other hand, in accordance with isoelectric focusing in which a polyacrylamide gel thin layer is used as a support medium, the fractionation of several samples at the same time is possible, the time required for the fractionation is reduced to ⅓ or less that of the case where the column is used, and the amount of the carrier ampholyte used is smaller than the case of the column, thereby reducing the cost required for operation, and, thus, this method is, as an analytical method, better than the column method. However, the use of a polyacrylamide gel thin layer as a support medium gives rise to the problems that a long period of time is needed for the production of the thin gel layer, and, since the gel is soft and breakable, care and skill are required for the operation. Furthermore, this method suffers from the defects that operation time and cost increase, and the layer shrinks considerably on drying.

If it would be possible to effect isoelectric focusing using a porous polymer film such as a cellulose acetate film as has conventionally been used in electrophoretic analysis, the above defects would be removed. However, with conventional porous polymer films such as a cellulose acetate film and the like, it has been impossible to effect isoelectric focusing because of their electroendosmosis. (See, for example, D. H. Leaback and A. C. Rutter, *Biochem. Biophys. Res. Commun.*, Vol. 32, pages 447 to 453 (1968. B).)

SUMMARY OF THE INVENTION

Accordingly, an object of the present invention is to provide a support of a porous polymer film for electrophoresis which is of low electroendosmosis and which can be used in isoelectric focusing.

Another object of the present invention is to provide a support for electrophoresis on which it is possible to coat a sample and which is suitable for isoelectric focusing.

A further object of the present invention is to provide a support for electrophoresis which is not breakable in effecting operations such as staining, decolorization, and the like, and which has excellent operational properties and is suitable for isoelectric focusing.

Still another object of the present invention is to provide a support for electrophoresis which is free from shrinkage on drying, easy to store, and suitable for isoelectric focusing.

Still a further object of the present invention is to provide a process for the production of such a support for isoelectric focusing.

These objects of the present invention are attained by employing a porous polymer film having an electroendosmosis factor of 0 to plus about 10 mm, the electroendosmosis factor being measured according to the method as hereinbelow described.

DETAILED DESCRIPTION OF THE INVENTION

The present invention provides a support for electrophoresis comprising a porous polymer film having an electroendosmosis factor of 0 to plus about 10 mm, and a process for the production of the same.

Figure 1:
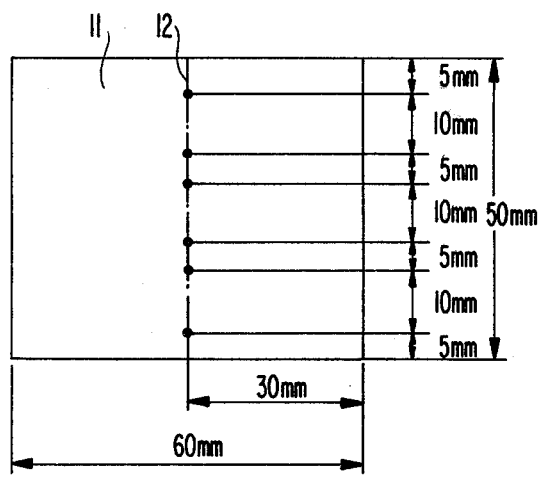
FIGS. 1 and 2 illustrate film samples for use in the method of measuring the electroendosmosis factor which indicates the extent of the electroendosmosis phenomenon in the present invention.
Figure 2:
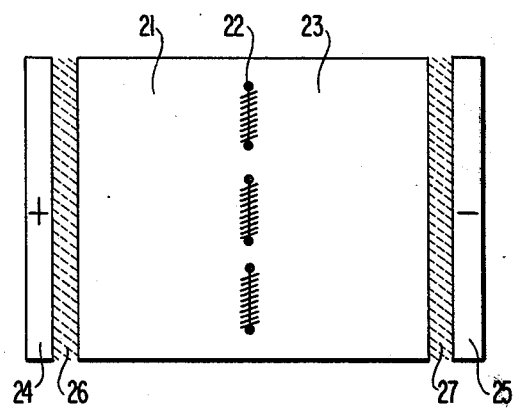

The above electroendosmosis factor is determined by the following method:

On a film sample cut to a rectangular size of 50 mm × 60 mm are put six marks 12 on the center line of the side 60 mm as shown in FIG. 1 by the use of a pencil. This film is dipped in a 0.07 M Veronal buffer solution (pH 8.60) having the following composition:
Diethyl Barbituric Acid — 2.17 g
Sodium Diethyl Barbiturate — 12.0 g
Water to make — 1 l After excess buffer solution on the surface is dried with filter paper, the film sample is set on a microanalysis electrophoretic apparatus Type 238 (produced by Joko Sangyo Co., Ltd.) with the same Veronal buffer solution as used above as an electrolyte. At the marks of the film sample so set, a 0.5% solution of Blue Dextran (Blue Dextran 2000, produced by Pharmacid Fine Chem. Co.) in water is coated in an amount of 1.6 μl/cm (wet basis) in such a manner that two marks are connected, as shown in FIG. 2, wherein 21 is a porous polymer film, 22 is a mark provided with a pencil, and 23 is the area where the Blue Dextran is coated. Thereafter the film sample is subjected to electrophoresis at a constant voltage of 15 v for 45 minutes.

After electricity has been passed for 45 minutes, the film sample is taken out, and then the distance and direction that the Blue Dextran moves from the position where it was coated are measured. The distance is expressed in "mm", and where it moves in the direction of the anode, the sign of "plus" is given, and in the case of moving in the direction of the cathode, the sign of "minus" is given. For instance, when it moves 3 mm in the direction of the anode, "plus 3 mm", and when it moves 3 mm in the direction of cathode, "minus 3 mm".

The average value of the three coating lines 23 shown in FIG. 2 in distance of movement and direction is defined as the electroendosmosis factor of the film sample.

This method is very convenient and makes possible to exactly determine the extent of the electroendosmosis of a film sample. Only those porous polymer films having an electroendosmosis factor of 0 to plus about 10 mm when measured by the above method enables one to effect the isoelectric focusing. Particularly those porous polymer films having an electroendosmosis factor of 0 to 5 mm are preferred.

The measurement of conventional cellulose acetate films with respect to the electroendosmosis factor reveals that Separax (produced by Fuji Photo Film Co., Ltd.) is about minus 20 mm. Since its electroendosmosis factor is minus, even though it is used as a support for isoelectric focusing, the pH gradient is disturbed due to the movement of the buffer solution towards the cathode due to the electroendosmosis, and, thus, it is impossible to effect isoelectric focusing in a good manner.

No porous polymer film conventionally used or known falls within the range of 0 to plus about 10 mm in its electroendosmosis factor.

To provide porous polymer films having an electroendosmosis factor of 0 to plus about 10 mm in the present invention, it is effective that nonionic surface active agents and/or cellulose ether, etc., be added to a mixed solution comprising at least one polymer material for the formation of a film and a solvent (the mixed solution is generally called a "dope").

The polymer material capable of constituting the porous polymer film of the present invention is a nonionic polymer which includes cellulose esters such as nitrocellulose, acetyl cellulose, acetyl butyl cellulose, cellulose propionate, and the like, a polyamide resin, a polyvinyl chloride resin, etc.

Of these polymer materials, cellulose esters and a polyamide resin are preferably used. In particular, acetyl cellulose is preferred.

Most preferred nonionic polymers for utilization in the present invention have a molecular weight of from about 10,000 to about 50,000, and, of course, are most preferably selected from the above cited preferred class.

In producing the porous polymer film, the above polymer material is first dissolved in a solvent.

The solvent as used in the present invention contains all of a good solvent, a poor solvent, and a non-solvent. Herein the term "good solvent" designates those solvents capable of dissolving the polymer materials; the term "poor solvent" designates those solvents which are mutually soluble with good solvents, do not substantially dissolve the polymer materials but only swell them, and have a higher boiling point than a good solvent; and the term "non-solvent" designates those materials which are mutually soluble with good solvents or poor solvents, do neither dissolve or swell the polymer materials, and have a higher boiling point than good solvents. While not to be construed as limitative, preferred good solvents have a boiling point of at most about 100° C., preferably 20° to 100° C., preferred poor solvents have a boiling point higher than the good solvents, most preferably from about 100° to about 300° C., even more preferably from about 100° C. to 150° C., and preferred non-solvents exhibit the same boiling point characteristics as the poor solvents.

Representative examples of good solvents are methylene chloride, acetone, methyl formate, and the like for acetyl cellulose; diethyl ether, methyl acetate, acetone, acetic acid, and the like for nitrocellulose; and methanol, ethanol, and the like for a polyamide resin, etc.

Representative examples of poor solvents are tetrahydrofuran, methanol, and the like for acetyl cellulose; butanol, ethanol, and the like for nitrocellulose; tetrahydrofuran, dioxane, ethyl acetate, and the like for a polyamide resin, etc.

As the non-solvent, water is often used. The main requirement of a useful non-solvent is, of course, that such should not swell or dissolve the polymer film, and must be soluble with the good and poor solvents. As indicated above, the boiling point is higher than that of the good solvent. While water is most preferred, polyhydric alcohols such as glycerin, ethylene glycol, etc., can also be used, if desired.

The good solvent and at least one solvent selected from the poor solvent and the non-solvent are mandatory in the process of the present invention.

No unequivocal line of demarcation amoung good solvents, poor solvents, and non-solvents can be made without knowing the polymer material. As can be understood from the above examples, good solvents for a certain polymer material are sometimes poor solvents or non-solvents for another polymer material. Also, mixtures of two or more solvents can be used as good solvents, or poor solvents, or non-solvents.

This relationship, however, is based upon the chemical and physical properties of the polymer material, and the choice of the polymer material, and three kinds of solvents can be easily be selected by one skilled in the art. Therefore, no further explanation will be needed.

The present invention is not especially limited in the fashion chosen for dissolving and mixing the polymer material, and good, poor, and non-solvents. A method in which a polymer material is dissolved in a good solvent and then poor and non-solvents are added; a method in which a polymer material is added to a mixture of a good solvent with a part of a poor solvent dissolved therein and the residual poor solvent is added to the solution prepared above, and, furthermore, a non-solvent is added thereto; and many other methods can all be used in the present invention. Other conditions such as the mixing ratio of each of the solvents, the temperature at which the mixing is carried out, etc., do not suffer from any limitations (although mixing should be carried out below the boiling point of the solvent(s) or non-solvent(s) used).

If the polymer solution prepared is stable, subsequent operations are simplified, and, therefore, the dissolving and mixing are desirably carried out in such a manner as to produce a stable solution. The term "stable solution" designates those solutions in which the polymer material is free from gellation and phase separation, and to obtain such a stable solution, techniques such as a method in which the amount of the good solvent in the solution is made larger than those of the other solvents, and a method in which the polymer material is added to a mixture of all of the good solvent and a part of the poor solvent, dissolved therein, and then the remaining poor solvent is added, etc., can be employed.

It is most preferred in accordance with the present invention that the good, poor and non-solvent be used at a mixing ratio of about 20 to about 80 wt% of the good solvent with from about 1 to about 20 wt% of the non-solvent, balance poor solvent (if any) 0 to about 60 wt%, based on 100 wt% of solvent (which term includes good, poor and non-solvents).

Mixing is conveniently performed at a temperature of from about 0° to about 100° C., even more preferably from 20° to 40° C. over a period of time of about 2–3 minutes to about 24 hours; time is not overly important, and can be widely varied. Generally, lower times are preferred from the viewpoint of process efficiency.

In the present invention, as one method of producing a porous polymer film having an electroendosmosis factor of 0 to plus about 10 mm, nonionic surface active agents are added to the above dope.

While nonionic surface active agents can, in general, be used with success in practicing the present invention, preferred are those nonionic surface active agents which have a molecular weight of from about 300 to about 50,000, even more preferably from 500 to 10,000. The following nonionic surface active agents are illustrative of those as can be used (while not to be construed as limitative, in the following any alkyl group preferably has from 1 to 30 carbon atoms, even more preferably from 4 to 20 carbon atoms):

polyethylene glycol alkyl ester, glycerine monoalkyl ester, sorbitan monoalkyl ester, saccharose ester, and the like;
polyoxyalkylene alkyl ether, polyoxyalkylene alkyl aryl ether, and the like;
polyoxyalkylene alkylamine, and the like;
polyoxyalkylene alkylamide, aliphatic ethanolamide, methylolamide, and the like; and
polyoxyalkyl sorbitan alkyl ester, polyoxyalkylene glycol alkyl ester, and the like.

Of these nonionic surface active agents, those nonionic surface active agents having a molecular weight of about 500 to about 10,000 are preferred, as indicated.

In particular, polyoxyalkylene alkyl aryl ether, and polyoxyalkylene sorbitan alkyl ester are preferred.

Polyoxyalkylene alkylaryl ether is represented by the following formula (I):

$$R(Ar)O(AO)_nH \quad (I)$$

wherein R is a branched or straight alkyl group containing 4 to 20 carbon atoms, e.g., butyl, t-butyl, octyl, γ-butyloctyl, and the like; Ar is a phenyl or naphthyl group; —AO— is an alkylene oxide group containing 2 or 3 carbon atoms, i.e., ethylene oxide or propylene oxide; and n is an integer of 5 to 100, preferably 15 to 50. Of those ones represented by formula (I), a polyoxyethylene alkylphenyl ether is particularly preferred.

Polyoxyalkylene sorbitan alkyl ester is represented by the following formula (II):

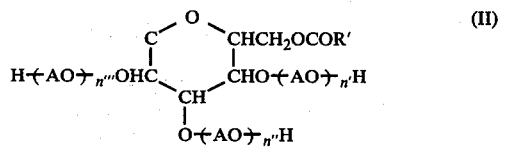

wherein —AO— is the same as defined above; R' is a branched or straight alkyl group, e.g., dodecyl, pentadecyl, heptadecyl, and the like; and n', n", and n'" are each integers of 5 to 100. Of those ones represented by formula (II), polyoxyethylene sorbitan alkyl ester is preferred.

Nonionic surface active agents available on the market are: Nissan Nonion, Nissan Naimin, and Nissan Naimide produced by Nippon Oil & Fats Co., Ltd., Emusol and Emulgen produced by Kao Soap Co., Ltd., Emulex produced by Japan Emulsion Co., Ltd., Emulox and Sumit produced by Yoshimura Oil Chemicals Co., Ltd., Noigen produced by Dai-ichi Kogyo Seiyaku Co., Ltd., and Livonox produced by Lion Oil & Fats Co., Ltd.

In the present invention, the amount of the nonionic surface active agent to be added is preferably about 1 to about 15% by weight based on the weight of the polymer material contained in the dope.

As one means for producing a porous polymer film having an electroendosmosis factor of 0 to plus about 10 mm, cellulose ether in combination with nonionic surface active agents may be added to the above dope and/or the nonionic surface active agents.

The cellulose ethers as used herein include those whose hydroxy groups are partly etherized, for example, methyl cellulose, ethyl cellulose, and the like. It is preferred that the methyl cellulose and ethyl cellulose preferably have an average molecular weight of about 60,000 to about 500,000, particularly 80,000 to 200,000. Particularly useful methyl cellulose and ethyl cellulose have an average degree of substitution of about 1.0 to 1.9. The term "degree of substitution" herein used designates how many hydroxy groups are contained in the cellulose (three hydroxy groups per one unit of cellulose) are substituted. For instance, if one hydroxy group is substituted by one methoxy group, the degree of substitution is 1. Cellulose ether of the present invention includes those ethers whose substituents are partly substituted by hydroxyalkoxy groups containing 1 to 3 carbon atoms, e.g., a hydroxypropoxy group, a hydroxyethoxy group, and the like (degree of substitution, about 0.1 to 0.3), etc.

The amount of the cellulose ether added is preferably about 0.1 to about 15% by weight based on the weight of the polymer material contained in the dope.

In producing the porous polymer film for electrophoresis of the present invention, those additives generally known in this art, e.g., plasticizers (for example, triphenyl phosphate, dibutyl phthalate), hydroscopic agents (for example, glycerin, ethylene glycol), auxiliary fine-pore forming agents (for example, inorganic salts such as zinc chloride, magnesium perchlorate), pore diameter controlling agents (for example, triacetin), and the like, may be added. It is most preferred that the amounts of any of the additives recited in this paragraph be from 0 to 50 wt% based on the film forming polymer, even more preferably (when used) from 1 to 20 wt%, for each type of additive, but that the total amounts of the additives be 50 wt% or less based on the film forming polymer.

From the thus prepared dope there can be produced a film by the methods as described in Japanese patent applications Nos. 28845/1974 and 677/1975.

The above production method is one example for obtaining the support for electrophoresis of the present invention.

Therefore, the support for electrophoresis of the present invention may be produced by methods other than the above method, and all porous polymer films exhibiting an electroendosmosis factor of 0 to plus about 10 mm are included in the support for electrophoresis of the present invention.

As the supports for electrophoresis of the present invention, those supports having a pore diameter of about $0.1\mu$ to about $10\mu$, voids of not less than 50%, and a thickness of about 30 to about $1,000\mu$ can be used, and particularly those supports having a pore diameter of 0.3 to $3.0\mu$, voids of 70 to 90%, and a thickness of 100 to $300\mu$ are preferably used. As used in the present specification, "voids" (V) is determined as follows:

Vacant space ratio $V = W/S$

Testing procedure: a sheet is immersed in water, and the amount of water contained in the sheet is measured, where $W$ = volume of water contained in the sheet and $S$ = volume of the sheet.

Supports for electrophoresis comprising the porous polymer materials produced according to the present invention are low in electroendosmosis, and have an electroendosmosis factor of 0 to plus about 10 mm when measured by the method of the present invention. Thus, it is possible to obtain a linear pH gradient by effecting isoelectric focusing using a carrier ampholyte, and, therefore, isoelectric focusing is possible.

The use of the supports for electrophoresis comprising the porous polymer films of the present invention enables one to fractionate a number of samples at the same time, and, furthermore, enables one to effect fractionation with a small amount of carrier ampholyte, thus reducing the cost of operation. Moreover, the supports for electrophoresis of the present invention are considerably strong as compared with conventional supports comprising a thin polyacrylamide gel layer. Particularly, since they have good heat stability and excellent dimensional stability, they can be preferably used in effecting exact isoelectric focusing.

The present invention will be illustrated in detail by reference to the following Examples. In the Examples, all parts are percent by weight unless otherwise indicated.

EXAMPLE 1

To a solution (dope) consisting of 3 parts of cellulose triacetate, 3 parts of cellulose diacetate, 2 parts of triacetin, 60 parts of methylene chloride, 28 parts of methanol and 4 parts of water was added 0.3 part of a polyoxyethylene nonylphenyl ether (number of polyoxyethylene units = 15; molecular weight: approximately 860) non-ionic surface active agent, Emulex NP-15 (produced by Japan Emulsion Co., Ltd.) to prepare a uniform solution.

This solution was flowed onto a glass plate to a thickness of 1 mm. The solution so flowed was first dried at 25° C., and, when the whole surface of the resulting film whitened, the film was peeled off the glass plate, set in a frame, and dried at 100° C. for 1 hour. The thus obtained film had a thickness of $150\mu$ and about 70% voids, and its average pore diameter was $0.4\mu$.

The thus obtained porous film had a plus 0.5 mm electroendosmosis factor when measured by the above described method.

EXAMPLE 2

To a solution consisting of 3 parts of cellulose triacetate, 3 parts of cellulose diacetate, 2 parts of triacetin, 60 parts of methylene chloride, 28 parts of water, and 4 parts of water was added 0.5 part of methyl cellulose (produced by Shin-etsu Chemical Industry Co., Ltd., Metholose SM 4000; average molecular weight 86,000) to produce a uniform solution. This solution was flowed and dried in the same manner as in Example 1, and a film was thus obtained which had a thickness of $150\mu$, about 80% voids, and an average pore diameter of $0.5\mu$.

The thus obtained film exhibited an electroendosmosis factor of plus 3.3 when measured by the above described method.

This film was cut to a size of 5 × 10 cm, dipped in a 2% Ampholine (produced by LKB in Sweden, pH 3.5 to 10) solution containing 10% sucrose, thereafter adhered to a glass plate and subjected to isoelectric focusing by the use of an isoelectric point electrophoretic apparatus (produced by Giaman Co., Ltd.) at 300 to 800 v for 2 hours. An electrode solution for the anode was provided by inserting between the electrode and the porous cellulose film a 6 × 60 mm filter paper soaked with a 0.5% phosphoric acid solution containing 20% sucrose, and that for the cathode was provided by inserting a 6 × 60 mm filter paper soaked with a 0.5% ethylenediamine solution containing 5% sucrose.

In the center of the film was coated a 1% hemoglobin solution in an amount of 1.6 $\mu$l/cm with a micropipette.

Figure 3:
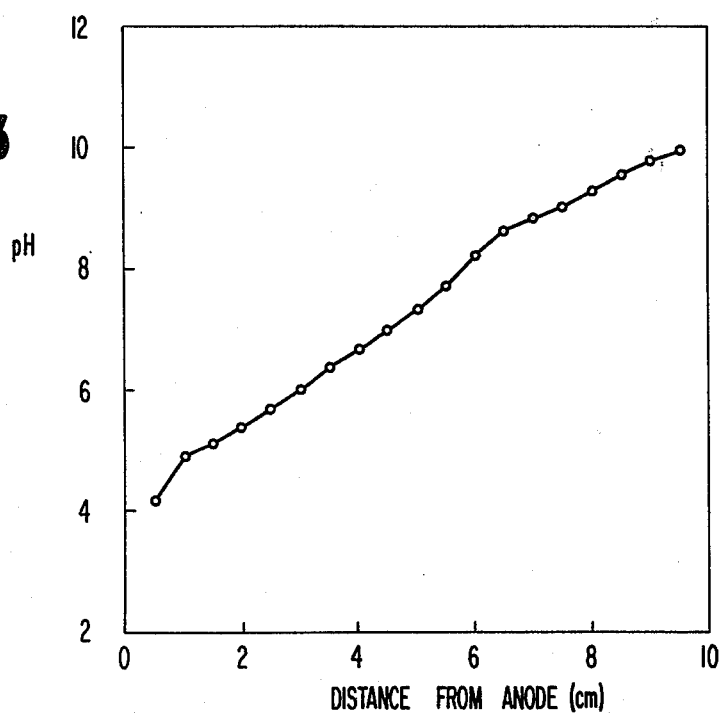
FIG. 3 illustrates the pH gradient obtained in Example 1.

As a result of isoelectric focusing, the above porous film fractionated the hemoglobin into 4 sections. Furthermore, when the pH gradient was measured with a micro pH electrode (produced by Fuji Kagaku Keisoku Co., Ltd.), a straight pH gradient was obtained as shown in FIG. 3.

EXAMPLE 3

In 50 parts of methanol and 23 parts of water was dissolved 16 parts of alcohol soluble nylon (soluble nylon CM-4000, produced by Toray Co., Ltd.), and, thereafter 10 parts of diethylene ether as an additive was added. Furthermore, 0.4 part of Emulex NP-15 (the same as used in Example 1) was added thereto to produce a uniform solution.

This solution was flowed over a glass plate and processed in the same manner as used in Example 1, whereby a porous nylon film was obtained.

The thus obtained film exhibited an electroendosmosis factor of plus 1.0 mm when measured by the above described method.

With this film, isoelectric focusing was conducted in the same manner as in Example 2, and a linear pH gradient substantially similar to that of Example 2 was thus obtained.

While the invention has been described in detail and with reference to specific embodiments thereof, it will be apparent to one skilled in the art that various changes and modifications can be made therein without departing from the spirit and scope thereof.

What is claimed is:

1. A support for electrophoresis comprising a porous polymer film having an electroendosmosis factor of 0 to plus about 10 mm, pore diameter of about 0.1 to 10 microns and voids of not less than 50%.

2. The support according to claim 1, wherein the polymer constituting the porous polymer film is a non-ionic polymer having a molecular weight of from about 10,000 to about 50,000.

3. The support according to claim 2, wherein the polymer constituting the porous polymer film is selected from the group consisting of nitrocellulose, acetyl cellulose, acetylbutyl cellulose, cellulose propionate, a polyamide resin, and a polyvinyl chloride resin.

4. A process for producing a support for electrophoresis comprising a porous polymer film having a pore diameter of about 0.1 to about 10 microns, an electroendosmosis factor of 0 to plus about 10 mm, and voids of not less than 50% which comprises adding 1 to 15% by weight of polymer of a nonionic surface active agent, a cellulose ether or a mixture thereof to a mixed solution comprising at least one polymer material for formation of a film and a solvent, and forming said porous polymer film from said mixed solution.

5. The process according to claim 4, wherein the solvent contains a good solvent for said polymer and at least one solvent selected from the group consisting of a poor and a non-solvent for said polymer, said good solvent being a solvent capable of dissolving the polymer material, said poor solvent being a solvent which is mutually soluble with said good solvent but does not substantially dissolve the polymer material but only swells the polymer material and has a higher boiling point than said good solvent, and the non-solvent being a solvent which is mutually soluble with good solvent or poor solvent, but neither dissolves nor swells the polymer material and has a higher boiling point than said good solvent.

6. The process according to claim 4, wherein the nonionic surface active agent has a molecular weight of about 500 to about 10,000.

7. The process according to claim 4, wherein the nonionic surface active agent is selected from the group consisting of polyoxyalkylene alkylaryl ethers and polyoxyalkylene sorbitan alkyl esters.

8. A support for electrophoresis comprising a porous polymer film which contains 1 to 15 weight percent of the polymer of a non-ionic surface active agent, a cellulose ether or a mixture thereof, said support having an electroendosmosis factor of 0 to plus about 10 mm, pore diameter of about 0.1 to about 10 microns and voids of not less than 50%.

9. The support of claim 8 wherein only cellulose ether is employed.

* * * * *